(12) United States Patent
Williams et al.

(10) Patent No.: US 9,144,754 B2
(45) Date of Patent: Sep. 29, 2015

(54) SYSTEM AND METHOD FOR THE AUTOMATION OF COLUMN AND MEDIA PACKING

(71) Applicant: GE HEALTHCARE BIO-SCIENCES CORP., Piscataway, NJ (US)

(72) Inventors: Alan M. Williams, Easton, PA (US); Kyril Dambuleff, Frenchtown, NJ (US); Kathryn Taylor, Flemington, NJ (US); John Davis, Singapore (SG); Adam Kaletski, Hillsborough, NJ (US); Daniel Go, Parsippany, NJ (US); Scott R. Muller, Montclair, NJ (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 0 days.

(21) Appl. No.: 14/089,042

(22) Filed: Nov. 25, 2013

(65) Prior Publication Data

US 2014/0076459 A1  Mar. 20, 2014

Related U.S. Application Data

(63) Continuation of application No. 12/526,050, filed as application No. PCT/US2008/050823 on Jan. 11, 2008, now Pat. No. 8,607,829.

(60) Provisional application No. 60/893,202, filed on Mar. 6, 2007.

(51) Int. Cl.
  *B65B 1/20* (2006.01)
  *B01D 15/14* (2006.01)
  *B01D 15/20* (2006.01)
  *G01N 30/56* (2006.01)

(52) U.S. Cl.
  CPC ............. *B01D 15/14* (2013.01); *B01D 15/206* (2013.01); *G01N 30/56* (2013.01); *G01N 2030/565* (2013.01)

(58) Field of Classification Search
  USPC ............... 210/656, 198.2; 73/61.53; 422/70; 141/12, 71, 73, 80, 94, 83
  See application file for complete search history.

(56) References Cited

U.S. PATENT DOCUMENTS

| | | | |
|---|---|---|---|
| 2003/0089662 A1* | 5/2003 | Hofmann | 210/656 |
| 2007/0012626 A1 | 1/2007 | Andersson et al. | |
| 2009/0007643 A1* | 1/2009 | Svensson et al. | 73/61.53 |

FOREIGN PATENT DOCUMENTS

| | | |
|---|---|---|
| EP | 1 859 847 | 11/2007 |
| WO | WO 2006/122824 | 11/2006 |
| WO | WO 2007/045491 | 4/2007 |

OTHER PUBLICATIONS

Hofmann, M., Journal of Chromatography A, 989 (2003) 79-94.

(Continued)

*Primary Examiner* — Jason K Niesz
(74) *Attorney, Agent, or Firm* — Parks Wood LLC; Collen A. Beard, Esq.

(57) ABSTRACT

This invention provides for the fully automated, hands free, packing of chromatography columns by means of delivering a pre-calculated volume of slurry and using two different packing modalities to stop the packing when either 1) this volume has been delivered in the column, or 2) when the adapter is moved to reach a bed height corresponding to the pre-calculated volume. Thus, a chromatography column can be packed in a fully automated fashion and such a column is 1) stable and 2) has the desired performance characteristic.

3 Claims, 6 Drawing Sheets

(56) References Cited

OTHER PUBLICATIONS

Sarker, M., et al., Journal of Chromatography A, 702 (1995) 27-44.
"Instructions 28-9064-05 AA: Capto adhere", Jan. 1, 2006, pp. 1-32, retrieved from the Internet: URL:http://wolfson.huji.ac.il/purification/PDF/IonExchange/AMERSHAM_CaptoAdhereInstruct.pdf [retrieved on Oct. 18, 2011].

* cited by examiner

SYSTEM AND METHOD FOR THE AUTOMATION OF COLUMN AND MEDIA PACKING

CROSS-REFERENCE TO RELATED APPLICATIONS

This application claims priority to U.S. provisional patent application No. 60/893,202 filed Mar. 6, 2007; the entire disclosure of which is incorporated herein by reference in its entirety.

FIELD OF THE INVENTION

The present invention relates to a media packing system for columns and media packing methods for use in columns. More specifically, the invention relates to packing devices and methods for improving the quality and consistency of packing chromatography media into chromatography columns.

BACKGROUND OF THE INVENTION

Columns used in liquid chromatography typically comprise a tubular body enclosing a porous chromatography medium through which a carrier liquid flows, with separation taking place by material collection between the carrier liquid and solid phase of the porous medium. Typically, the medium is enclosed in the column as a packed bed formed by consolidating a suspension of discrete particles, known as slurry that is pumped, poured, or sucked into the column. Consolidation of the slurry into a packed bed is achieved by compressing the slurry so that it is packed into a volume, which is less than the volume that it would have occupied if it had been allowed to settle under the influence of gravity to form a sedimented bed. The efficiency of subsequent chromatographic separation relies strongly on 1) the liquid distribution and collection system at the fluid inlet and outlet of the packed bed, 2) on the special orientation (also know as the packing geometry) of the media particles in the packed bed, and 3) on the compression of the packed bed. If the compression of the packed bed is too low then chromatographic separations performed on that bed suffer from "tailing" and, generally, such insufficiently compressed beds are unstable. If the compression of the packed bed is too high then chromatographic separations performed by the bed suffer from "leading" and such over-compressed beds can affect throughput and binding capacity, and, in general, give much higher operating pressures. If the compression is optimum, then the separation peaks formed during use exhibit much less leading or tailing and are substantially symmetrical. The optimum degree of compression required for a column is determined experimentally for each column size (width or diameter), bed height, and media type.

Prior to any separation process, the bed has to be prepared by starting from the slurry of particles that has to be introduced into the column. The process of bed formation is called 'the packing procedure' and a correctly packed bed is a critical factor influencing the performance of a column containing a packed bed. One of the primary goals of the packing procedure is to provide a bed, which is compressed by the optimum amount of compression, i.e. the optimum compression factor. The height of the bed when it is optimally compressed is called the target compressed bed height.

Large-scale columns, such as CHROMAFLOW™ (which is a registered trademark of GE Healthcare are columns manufactured by GE Healthcare in Piscataway, N.J.), CHROMAFLOW™-like columns and other columns presently utilized in the industry, are preferably packed by delivering it into the column, through a central slurry nozzle, media valve, or another port, a predetermined volume of slurry having a specified concentration of media particles. Once the predetermined volume of slurry has been delivered into the column, the chromatography medium in the column may be either 1) fully packed or 2) not packed and in need to be further consolidated and compressed by moving a movable adapter down the longitudinal axis of the column towards the bottom of the column, normally at a constant speed. The excess liquid during this procedure is expelled at the column outlet, while the media particles are retained by means of a filter material, a so-called 'bed support', with pores too small to allow the media particles to pass though. The packing process is complete once the packed bed has been compressed by the optimum amount or degree of compression. The packing process is considered successful if the compressed bed allows for a good and robust chromatographic performance. However, packing such an optimally compressed bed of chromatography media in a chromatography column by manual means is not easy to accomplish in practice due to the fact that the quality of the final packed bed depends to a great extent on the skill of the operator. During filling and subsequent packing of the column, the operator manually selects and adjusts all packing parameters such as valve positions, pump speed, flow rates, adapter's speed of movement, etc. More importantly, in all cases, the operator has to arbitrarily decide when the column packing should end by visually determining that either 1) sufficient slurry has been delivered into the column or 2) that the adapter has sufficiently compressed the bed. Mistakes in the selection of any of the packing parameters, and/or mistakes in the decision on when to end the packing, normally lead to a poorly performing column. Further, in columns equipped with a transparent tube it is particularly difficult, and in columns equipped with a non-transparent tube such as stainless steel it is impossible, to judge by eye when compression of the bed actually starts and a significant error at this point makes it impossible to obtain an optimally compressed bed. In sum, column packing has hitherto been regarded as an art rather than a science.

Therefore, there is a need for a system and method for the accurate and reproducible packing of chromatography media into chromatography columns.

SUMMARY OF THE INVENTION

The object of the invention is to provide a column packing system and a method for packing media into columns in order to overcome the drawbacks of the prior art systems.

This invention provides for the fully automated, hands free, packing of chromatography columns by means of delivering a pre-calculated volume of slurry and using two different packing modalities to stop the packing when either 1) this volume has been delivered in the column, which is the preferred modality for columns equipped with fixed adapters, or 2) when, after delivery of the pre-calculated volume of slurry, the adapter is moved to reach a bed height corresponding to the target compressed bed height, which is the preferred modality for columns equipped with movable adapters. Thus, a chromatography column can be packed in a fully automated fashion and such a column is 1) stable and 2) has the desired performance characteristic.

BRIEF DESCRIPTION OF THE DRAWINGS

These and other advantages of the present invention will become more apparent as the following description is read in conjunction with the accompanying drawings, wherein.

DETAILED DESCRIPTION OF THE INVENTION

The presently preferred embodiments of the invention are described with reference to the drawings. The descriptions of the preferred embodiments are exemplary and are not intended to limit the scope of the invention.

As used herein and in the appended claims:

The term "cell" is intended to include the terms "vessel" and "column", as well as any other structure utilized by practitioners of the separation arts, to effect a separation, and/or reaction, and/or catalyzation, and/or extraction of components from an admixture by bringing the admixture into contact with solid or liquid exchange media, known as the packed bed.

The term "longitudinal direction of flow" refers to the direction of flow from an inlet towards an outlet within a cell. "Longitudinal" is used consistently to designate the dominant flow path of fluid through a cell without regard to direction.

The term "flow connection system" refers to a system of channels or paths that connect two points in a fluid circuit.

The term "distribution system" refers to structures through which fluids are introduced to a cell and the term "collection system" refers to structures used to collect fluids from a cell.

The term "sedimented bed height" refers to the height of a bed of media particles which are obtained when a liquid and media particles in a column are allowed to sediment under the influence of gravity only—such a bed is called a "sedimented bed".

The term "consolidated bed height" refers to the height of a bed of media particles that is obtained when a bed of media particles is formed in a column while the media particles in a slurry are forced to sediment when a flow of fluid is applied through the slurry either by 1) pumping liquid into the column, 2) by pumping liquid out of the column, or 3) by the movement (for example, the descent) of a movable adapter, which forces liquid out of the column—such a bed is called a "consolidated bed".

The term "compressed bed height" refers to the height of a bed of media particles in a column that is obtained when a consolidated bed has been compressed, for example by contact with, and further movement of, a movable adapter or the like, or by pumping fluid through the column at a higher rate than that used during consolidation of the bed—such a bed is called a "compressed bed".

A First Automated Column and Media Packing System and Method

Figure 1:
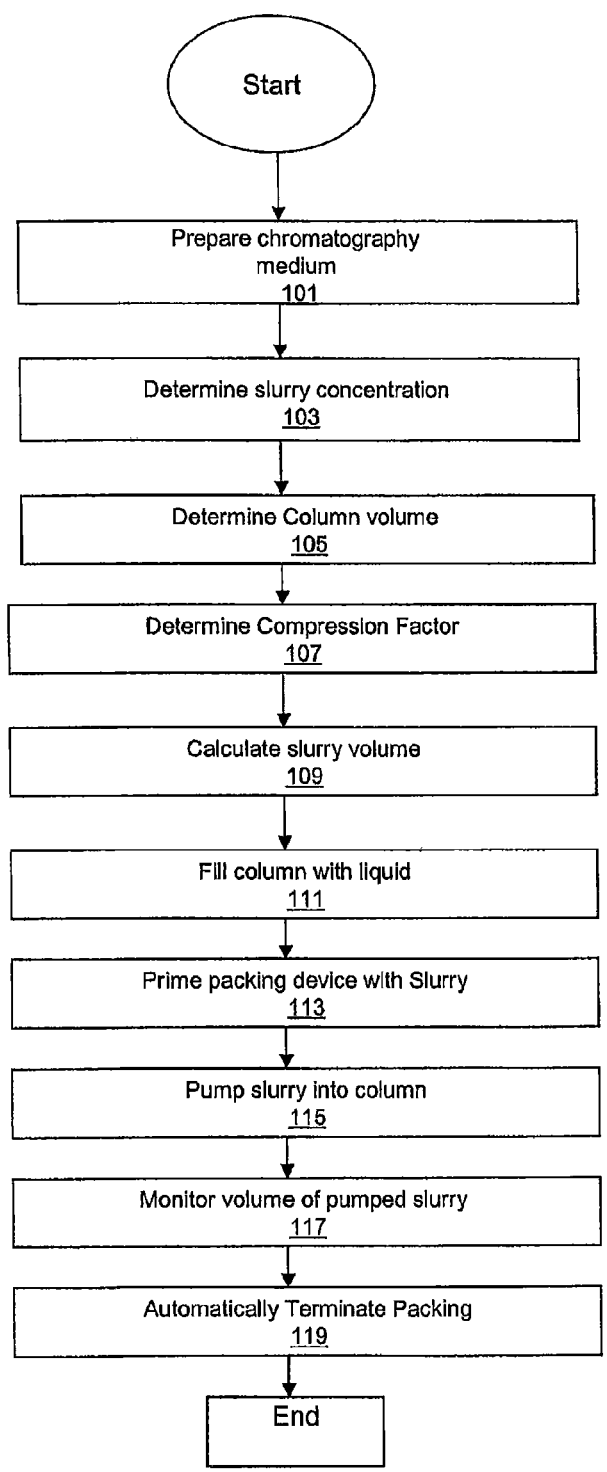
FIG. 1 depicts a flow-chart of a first automated column and media packing procedure in accordance with the invention.

FIG. 1 shows a flow-chart of a first automated column and media packing procedure. At block 101, the chromatography medium preparation occurs where any typical chromatography medium is suspended. The chromatography medium may also be referred to as gel, beads or resin. This suspension of the chromatography medium is achieved in the chromatography medium's shipping container (not shown) by the typical methods such as hand stirring, motorized agitation, aeration, shaking or vibration or using a MEDIA WAND™ (which is a GE trademark of a tool that is manufactured by GE Healthcare in Piscataway, N.J.). The MEDIA WAND™ is a robust, easy to use, and designed for removal of supernatant, addition of water or buffer, creation of homogenous media slurries in shipping containers and transfer of media to slurry tanks. The MEDIA WAND™ is a tool described in the United States patent application entitled "METHOD AND APPARATUS FOR FORMING AN HOMOGENEOUS MIXTURE OF CHROMATOGRAPHY MEDIA IN A VESSEL", which has a U.S. patent application Ser. No. 11/669,347 and it was filed Jan. 31, 2007, which is herein incorporated by reference.

Next, at block 101, the suspended chromatography medium is pumped from the chromatography medium's shipping container into a slurry tank 301 (FIG. 3) The slurry could be pumped using typical pumps, which are not damaging to the beads, such as diaphragm pumps or rotary lobe pumps. These typical pumps are usually located in between the chromatography medium container and the slurry tank(s) 301 or they may be incorporated in a packing station such as 303 (FIG. 3) or some another slurry-handling device such as the Media Handling Unit, which is a tool manufactured by GE Healthcare in Piscataway, N.J. The MEDIA WAND™ and Media Handling Unit are designed to simplify the handling of bulk media, thereby reducing handling time and work effort. Alternatively, the slurry could be physically poured out of the chromatography medium's shipping container and into the slurry tank 301 (FIG. 3) via an opening on top of the tank. The amount of chromatography medium contained in the slurry is generally referred to as the % slurry and also as slurry concentration. Both the percent slurry and slurry concentration reflect the volume of gravity settled (Vgs) material or solids (i.e. gel, chromatographic media, beads, resin) in the total slurry volume. The slurry concentration can be adjusted but is normally in the range of 25% to 75% Vgs in the total slurry volume. When the slurry is in the slurry tank 301, it is kept suspended by the standard means of agitation to ensure a homogeneous suspension, slurry or dispersion.

Figure 3:
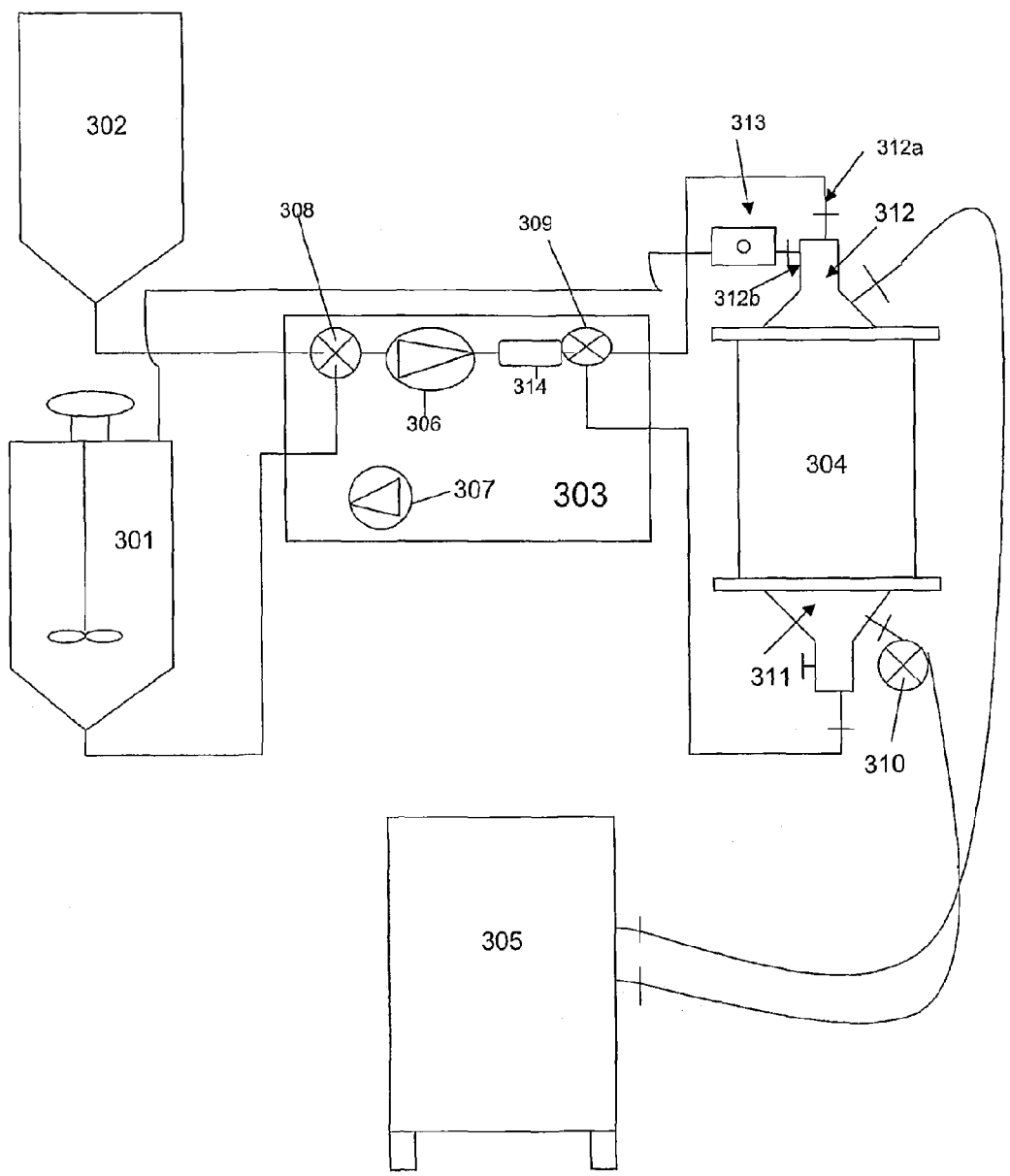
FIG. 3 is a schematic diagram of the first automated column and media packing system associated with FIG. 1 in accordance with the invention.

At the completion of the slurry preparation described above, a small sample of slurry may be removed from the slurry tank 301 (FIG. 3) utilizing a typical sample port that is a common feature in slurry tanks. Alternatively, a small sample of the slurry may be removed by simply scooping it out or by using a typical pipette. The actual sample volume removed from the slurry tank 301 is typically less than 1 liter, but may preferably be less than 0.1% of the column volume of the column 304 (FIG. 3).

Next, at block 103 (FIG. 1), the slurry concentration (SC) is determined by any one of the following techniques:

1. Sedimentation occurs whereby the slurry is allowed to settle fully under the force of gravity for a period of time sufficient for a complete sedimentation to take place. This time period varies with the type of chromatography media used and, in general, could range from 2 to 72 hours. For example, a 100-milliliter sample is withdrawn from the slurry tank 301 (FIG. 3), placed into a 100-milliliter graduated cylinder, and allowed to fully settle or sediment under gravity. If the fully sedimented bed then comes to a volume of 53 milliliters when read against the graduation marks on the graduated cylinder, the slurry concentration is said to be 53%.

2. Centrifugation occurs whereby the slurry is forced to settle under centrifugal forces. For example, a 100-milliliter sample is withdrawn from the slurry tank 301 (FIG. 3) and placed into a 100-milliliter graduated centrifuge tube. The tube is then placed in a centrifuge and the centrifuge is operated at 3000 RPM for 15 minutes. The tube is then taken out of the centrifuge and the volume of the sedimented bed is read against the graduation marks on the centrifuge tube and if that reading is 53 milliliters then the slurry concentration is said to be 53%.

3. Filtration occurs whereby the slurry is poured into a graduated cylinder, or some other graduated vessel, which is equipped with a filter that allows for the liquid in the slurry to be drained out but retains the media particles. For example, a 100-milliliter sample is withdrawn from the slurry tank 301 (FIG. 3), placed into a 100-milliliter graduated cylinder equipped with a filter or sinter at the bottom, and allowed to fully drain. If the sedimented bed then comes to a volume of 53 milliliters when read against the graduation marks on the modified graduated cylinder, the slurry concentration is said to be 53%.

4. Other means or methods, which utilize such principles or devices, such as light scattering, ultrasound, and particle counters, etc. For example, the other method may be a filtration method, but the liquid is not drained out the bottom of the column. In this case, a specific amount of slurry is poured into a column and the media is settled by a low flow through the column. When the bed is settled, then the bed is allowed to relax for a specific period of time. The height of the bed is measured and related to the height of the slurry originally filled. This aforementioned filtration method is further described in Swedish Patent application entitled "DETERMINATION OF SLURRY CONCENTRATION," with a Swedish Patent Office application number 0701671-0 filed on Jul. 6, 2007, which is herein incorporated by reference.

Next, at block 105 (FIG. 1), the column volume (Vc) of column 304 (FIG. 3) is determined. In a preferred embodiment of the invention, the column volume is determined empirically by filling the column 304 (FIG. 3) with water and then draining, collecting, and weighing the water. In another embodiment of the invention, the Vc of column 304 (FIG. 3) is determined by calculation as follows: Vc equals the cross-sectional area of the column $\Pi r^2$ multiplied by the column's height (L):

$$Vc = \Pi r^2 \times L.$$

The height at which the bed of chromatography medium is to be packed in a column is a well-defined, application-dependent, and controlled parameter, which is normally specified in the license to manufacture and cannot be deviated from. It is typically expressed as a set number within a certain range. For example, the column bed height for a particular application may be specified as 20+/−2 cm.

Figure 5:
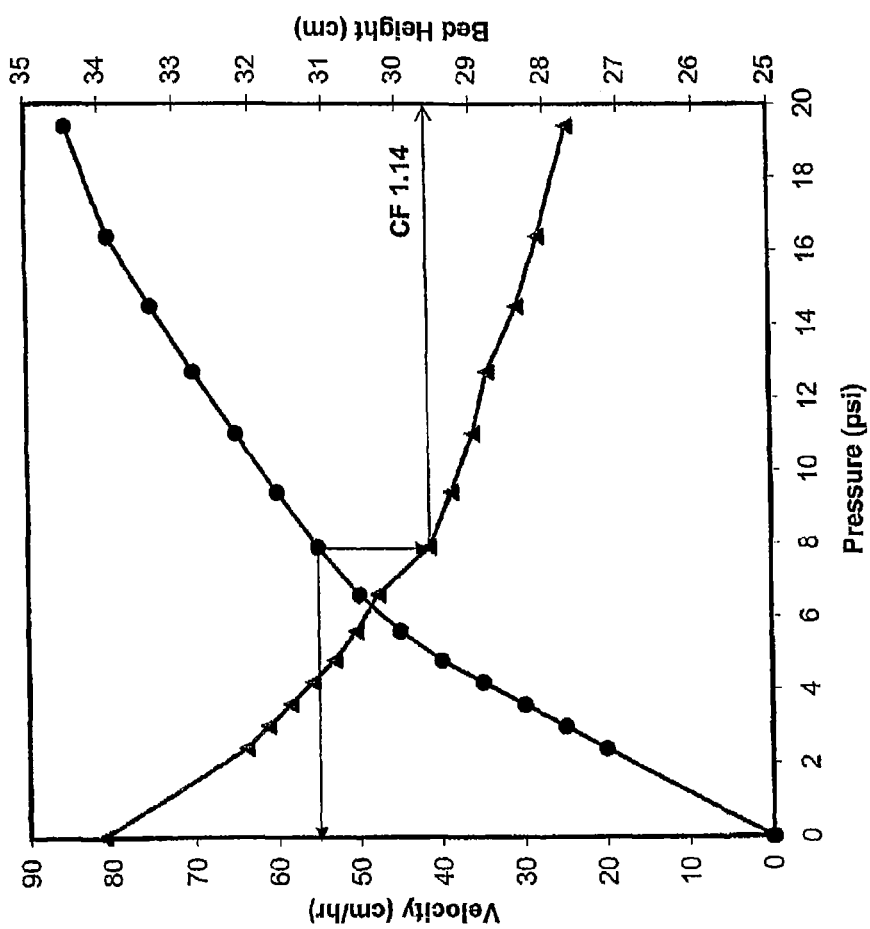
FIG. 5 is a graphical representation of a pressure flow curve and compression curve in accordance with the invention.

Next, at block 107, a compression factor (CF) is determined FIG. 5 shows the pressure-flow curve and the compression curve utilized to obtain the compression factor at which the bed of chromatography medium is to be packed in a column. The compressibility of a chromatography medium and the maximum flow rate (flow velocity) which can be attained when liquid is pumped through that medium when it is packed in a column at a particular bed height (i.e. the distance between the bottom and top of the bed) can be determined as follows: A volume of slurry (a mixture of water or other liquid and a chromatography medium, gel, resin, etc) is poured or pumped into a chromatography column, whose bottom outlet is closed, and is allowed to settle fully by gravity. The volume occupied by this settled chromatography medium is defined as gravity-settled volume and is given the symbol Vgs. The height of this settled gel bed is then recorded. In this example, this bed height could be referred to as "initial bed height". Using a pump, or another liquid-delivery device or equipment, a liquid is pumped through the column at incrementally higher flow rates. This continues until a maximum (also referred to as critical) flow velocity is reached at which point no higher flow velocity through the gel bed can be attained regardless of effort. The pressure (the resistance of the gel bed to the applied flow) and the bed height are recorded for each flow rate value. In general, the higher the flow rate applied to the column, the higher the pressure and the lower the bed height. Using the recorded values for flow rate, pressure, and bed height, two curves can be constructed:

CURVE 1 denoted by the circles on a line, which shows the relationship between pressure and flow velocity; and CURVE 2 denoted by the triangle on a line, which shows the relationship between pressure and bed height.

As can be seen from the chart in FIG. 5, for every flow velocity there are corresponding pressure and bed height. Thus, the compression factor (CF) can be derived using the formula:

$$CF = (\text{initial bed height})/(\text{bed height at flow}).$$

For example, the compressibility or Compression Factor (CF) of this chromatography medium at the maximum flow velocity can be determined by dividing the "initial bed height" of 34 cm by the "final bed height" of 27.7 cm. i.e. 34/27.7=1.23. The chart in FIG. 5 shows a compression factor of 1.14 for this particular gel at a flow velocity of 55 cm/h.

Also, the compression factor may be viewed as the decrease in the height of the chromatography medium in a column from an initial value when the chromatography medium or gel is settled by gravity (Vgs) to a final value when the chromatography medium is compressed by flow close to a maximum flow velocity. The compression factor value should not be thought as a set value deviation from which is undesirable, but rather as a range in which optimum column performance could still be achieved. For example, if a chromatography medium compresses by a factor of 1.15, optimum column performance could still be attained in the range of 1.12 to 1.18. By another example, if a chromatography medium compresses by a factor of 1.20, optimum column performance could still be attained in the range of 1.16 to 1.24, etc.

Next, at block 109 the volume of the slurry (Vs) needed for packing the column 304 (FIG. 3) is calculated. This is the slurry volume required for the appropriate Vgs to be delivered into column 304 and compressed to the determined compression factor or desired compression factor, within a desired compression factor range, and this Vs can be calculated by hand. In another embodiment of the invention, the volume of slurry needed for packing may be calculated by the control unit 305 or by a separate computer (not shown). Control unit 305 (FIG. 3) is a typical computer that includes a processor that is able to calculate the volume of the slurry (Vs) based on an equation.

Figure 4:
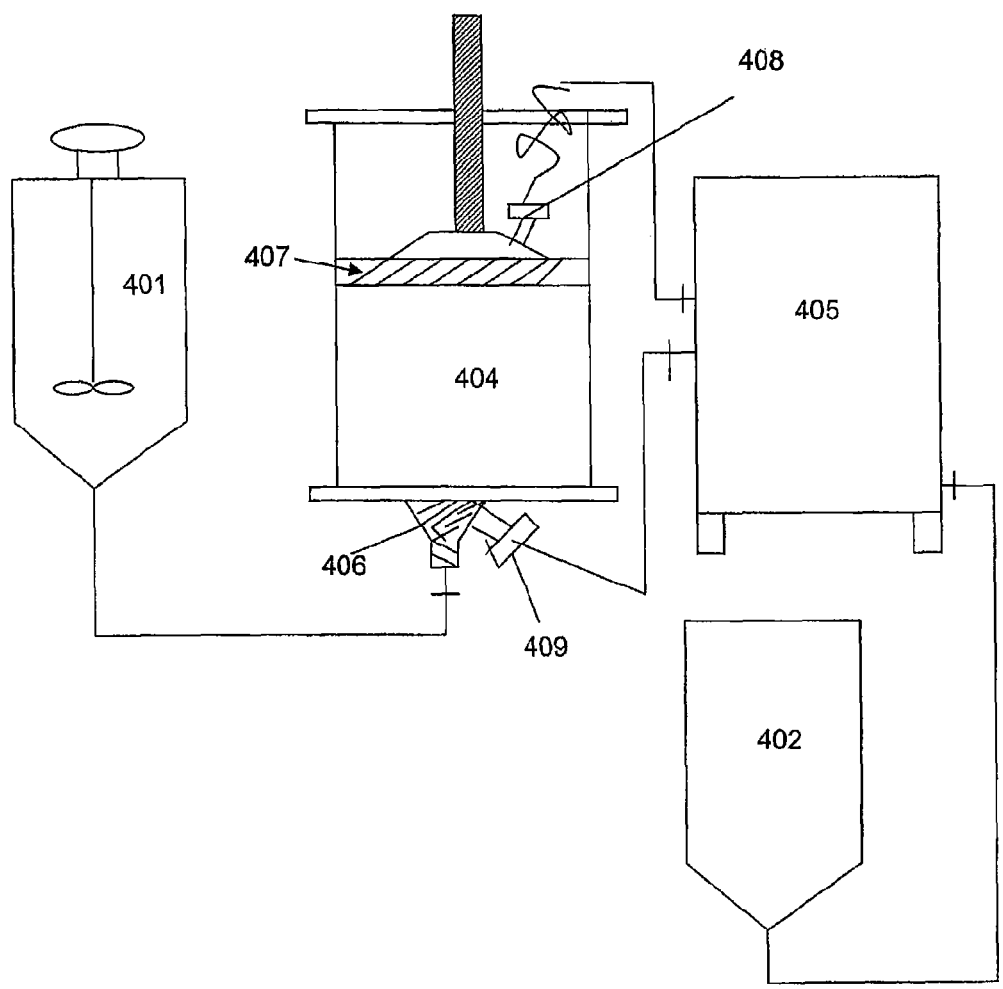
FIG. 4 is a schematic diagram of the second automated column and media packing system associated with FIGS. 2A and 2B in accordance with the invention.

Control unit 305 as a typical computer includes the standard components: a processor, an input/output (I/O) controller, a mass storage, a memory, a video adapter, a connection interface and a system bus. The mass storage includes: 1. a hard disk drive component (not shown) for reading from and writing to a hard disk and a hard disk drive interface (not shown), 2. a magnetic disk drive (not shown) and a hard disk drive interface (not shown) and 3. an optical disk drive (not shown) for reading from or writing to a removable optical disk such as a CD-ROM or other optical media and an optical disk drive interface (not shown). The aforementioned drives and their associated computer readable media provide non-volatile storage of computer-readable instructions, data structures, program modules and other data for the control unit 305. Also, the aforementioned drives include the technical effect of having an algorithm for a first automated column and media packing procedure which is described in FIG. 1. The algorithm may also be software or equation of the procedure illustrated in FIG. 1. Referring to FIG. 4, a control unit 405 (FIG. 4) is equivalent to control unit 305 that has the aforementioned drives, which include the technical effect of having an algorithm for a second automated column and media packing procedure which is described in FIG. 2. This algorithm for the second automated column and media packing may also be software or equation of the procedure illustrated in FIG. 2.

Referring to FIG. 3, the control unit 305 includes hardware and software for controlling the operation of column 304. Further, control unit 305 controls and communicates with all equipment units utilized in the automated column packing such as valves, pumps, air sensor, pressure transducer, flow meter, etc. In order to calculate the volume of slurry (Vs) the following equation is utilized:

$$Vs = (Vc \times CF)/Cs.$$

The volume of the slurry is equal to the column volume (Vc) multiplied by the compression factor (CF) that is divided by the slurry concentration (Cs). The required volume of slurry is prepared in the slurry tank 301 and an additional volume of slurry may be added to allow for the external volume between the slurry tank 301 and the column 304 including a packing station 303 and hoses. The packing station 303 is a typical packing station that includes pumps 306 and 307 and valves 308 and 309 needed for slurry delivery.

Next, at block 111 (FIG. 1), the packing station 303 (FIG. 3) applies liquid from tank 302 to the column 304 (FIG. 3) via pump 306 (FIG. 3) and via nozzle 311 (FIG. 3), which is inserted into pack position. As column 304 is filled with liquid, air from inside it is vented via nozzle 312 and passes through an air sensor 313 (FIG. 3). Air sensor 313 is a typical air sensor that is connected to, and in communications with, the control unit 305. The air sensor 313 either determines if there is or is not air moving through it and this capability is used to establish when the column is filled with water at which point the control unit 305 can automatically proceed to the next block.

At block 113 (FIG. 1), the control unit 305 (FIG. 3) controls the packing station 303, where the control unit 305 automatically primes the packing station 303, slurry lines, hoses and nozzle 312 with slurry by recycling slurry from the slurry tank 301 through the packing station 303, nozzle 312 and slurry lines back to the slurry tank 301. This priming action occurs by the nozzle 312 being in the retracted or closed position whereby a loop is formed between a slurry inlet (SIT) 312a and waste slurry port (SOT) 312b, where the slurry is sent through the slurry inlet (SIT) 312a and dispersed through the waste slurry port (SOT) 312b and associated hoses back to the slurry tank 301. Once this priming has been accomplished, the control unit 305 proceeds automatically to the next block.

At block 115 (FIG. 1), the control unit 305 (FIG. 3), which is connected to and in communication with all critical components, performs the following: 1) zeroes the flow meter 314, 2) positions the nozzle 312 in the packing or open position which allows for the delivery of the slurry in the column 304 that is water-primed, 3) opens the column's 304 bottom outlet by operating valve 310, and 4) starts the packing pump 306 (FIG. 3), which delivers the chromatography medium into the column 304. Thus, the packing of the column has been initiated.

At block 117 (FIG. 1), the control unit 305 (FIG. 3), which is connected to and in communication with the flow meter 314, controls the flow meter 314 to monitor the volume of slurry pumped into the column 304, where the flow meter 314 communicates to the control unit 305 the monitored volume of slurry pumped into the column 304.

Next, at block 119 (FIG. 1), the processor in the control unit 305 (FIG. 3) automatically terminates the packing of the column 304 when the monitored volume measurement of slurry pumped into the column 304 is equivalent to the pre-calculated slurry volume (Vs), which was determined in block 105 (FIG. 1). The control unit 305 then performs the following: 1) stops the packing pump 306, 2) retracts or closes the nozzle 312, and 3) closes the mobile phase inlet/outlet of the column 304 by operating valve 310. In another preferred embodiment of the invention, the volume of slurry pumped into the column 304 can be monitored via a connection and communication between the control unit 305 and the slurry tank 301, which itself can be equipped with a volume measuring device either internal or external. In yet another preferred embodiment of the invention, the volume of slurry pumped into the column 304 can be monitored via a connection and communication between the control unit 305 and a scale on which the slurry tank 301 is placed.

The Second Automated Column and Media Packing System and Method

Figure 2A:
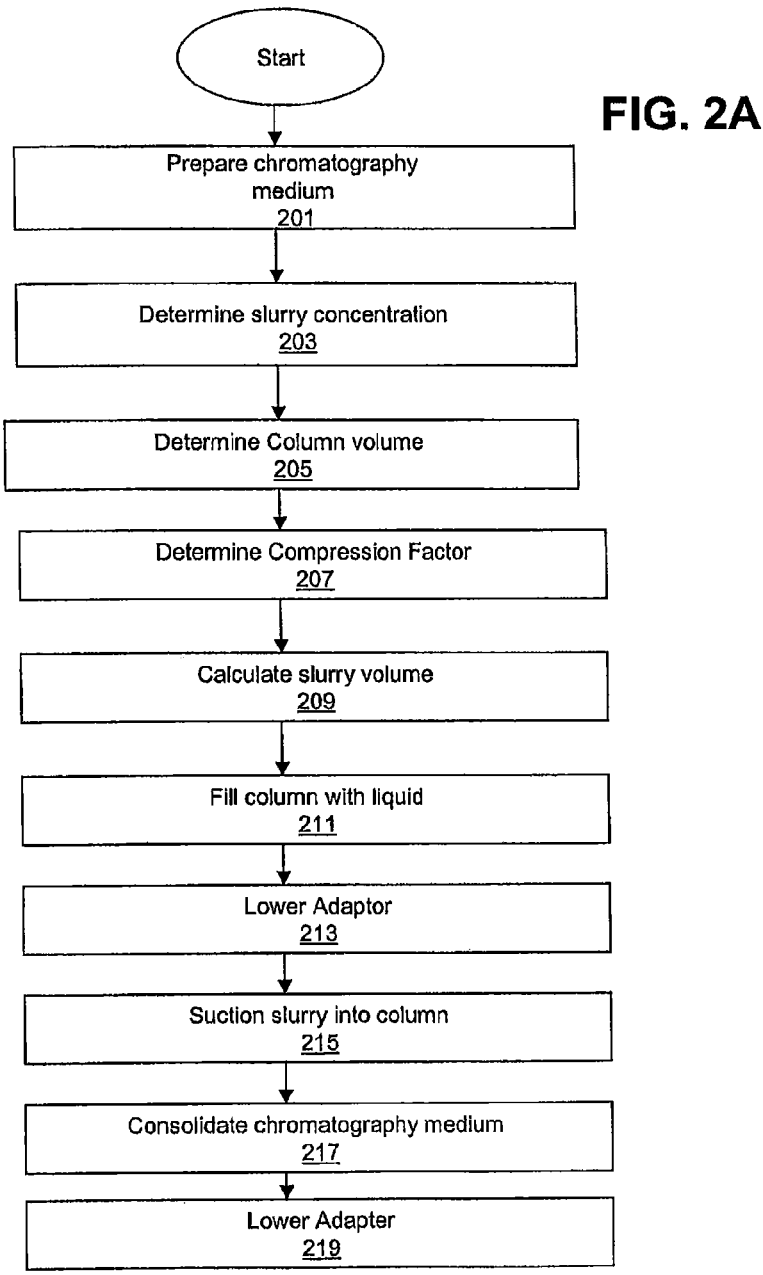
FIGS. 2A and 2B depicts a flow-chart of a second automated column and media packing procedure in accordance with the invention.
Figure 2B:
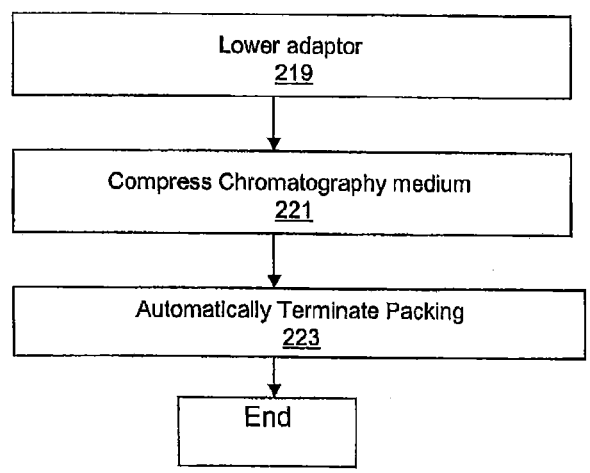

FIGS. 2A and 2B shows a flow-chart of the second automated column and media packing procedure. This flow-chart includes blocks 201 to 211 (FIG. 2A) where the procedures are equivalent and described in blocks 101 to 111 so a description of these blocks will not be disclosed here.

At block 213, the control unit 405 (FIG. 4), which is connected to and in communication with all critical components, moves the adapter 407 (FIG. 4) downwards either by mechanical, electrical, or hydraulic means to the point where the adapter is at it's lowest position where either a known volume of the liquid used for priming remains in the column 404 or no liquid at all remains in the column 404.

At block 215 (FIG. 2), the control unit 405 (FIG. 4), which is connected to and in communication with all critical components, performs the following: 1) positions or opens the media valve (also referred to as nozzle, slurry valve or slurry port) 406 which allows for the delivery of the slurry in the column 404 (FIG. 4) that is water-primed, and 2) moves the adapter 407 (FIG. 4) upwards either by mechanical, electrical, or hydraulic means. Control unit 405 is equivalent to the control unit 305 described above so it will not be described here. As the adapter 407 is moved, slurry is sucked from the slurry tank 401 (FIG. 4) into the column 404 via the nozzle 406. This process of suction of slurry into the column 404, which is operated essentially in a syringe-like fashion, can be assisted, if necessary, by positive pressure in tank 401. The control unit 405 monitors the adapter's height either by the standard mechanical, electronic, or hydraulic means (not shown) and stops the adapter 407 when the adapter 407 has moved to a height corresponding to the pre-calculated slurry volume (Vs) needed for packing at which point a volume of slurry equal to Vs has been delivered into the column.

Next, at block 217 (FIG. 2A), the control unit 405 (FIG. 4) by means of either an internal or external pump (not shown) causes water or buffer from tank 402) to be pumped into the column 404 (FIG. 4) at a pre-determined flow rate via the column's mobile phase ports 408 and 409 (FIG. 4). The chromatography medium, which at this point is in the form of slurry inside the column 404, is consolidated under this flow and the control unit 405 continues to apply flow through the column 404 until the bed is consolidated and a water layer (gap) is created and stabilized between the movable adapter 407 and the chromatography medium bed Next, at block 219 (FIG. 2A), the movable adapter 407 (FIG. 4) is automatically lowered by the control unit 405 to the top of the chromatography medium bed after either 1) monitoring the volume of liquid evacuating from the column 404 via either mobile phase port 408 or 409 when the movable adapter 407 is lowered in a syringe-like fashion, or 2) by monitoring the movable adapter's 407 height.

Next, at block 221 (FIG. 2B), the movable adapter 407 (FIG. 4) is further automatically lowered by the control unit 405 in order to compress the chromatography medium to the pre-determined and desired compression factor after either 1) monitoring the volume of liquid evacuating from the column 404 via either mobile phase port 408 or 409 when the movable adapter 407 is lowered in a syringe-like fashion, or 2) by monitoring the movable adapter's 407 height.

Next, at block 223 (FIG. 2B), the control unit 405 (FIG. 4) automatically terminates the packing of the column 404 when an optimal height is reached. The optimal height occurs when the moving adapter 407 has displaced a volume of liquid equal to the difference in volume between the adapter's 407 initial height (the height at end of block 215) and the adapter's 407 final height, from the column 404 which value is known to the control unit 405 and is monitored by a flow meter (not shown) in a fashion similar or identical to the one already described. In another embodiment of the invention, the control unit 405 automatically terminates the packing of the column 404 when a bed-height reading device or any other device capable of determining the adapter's position (not shown), which is connected to and in communication with the control unit 405, reaches a value equal to the desired final packed column height that has a value known to the control unit 405.

In another embodiment of the invention, starting at block 217 and ending with block 223, consolidation of the chromatography medium in the column 404 can be accomplished by means of moving the adapter 407 either mechanically, electrically, or hydraulically by the standard operation and by opening either mobile phase port 408 or mobile phase port 409 until a desired consolidation is achieved. If this embodiment becomes the chosen mode of execution of the automated packing procedure, then block 219 can be skipped and the automated packing procedure can proceed through block 221 and be automatically terminated at block 223 exactly as described above.

In yet another preferred embodiment of the invention, starting at block 217 and ending with block 223, consolidation and subsequent compression can be accomplished in a single step by means of moving the adapter 407 either mechanically, electrically, or hydraulically by the standard operation and opening either mobile phase port 408 or mobile phase port 409 until both the desired consolidation and compression are achieved. If this embodiment is the chosen mode of execution of the automated packing procedure, then block 219 and block 221 can both be skipped and the automated packing procedure can proceed directly to, and be automatically terminated in, block 223 exactly as described above.

This invention provides a fully automated system and method for packing chromatography columns by means of delivering a pre-calculated volume of slurry. The user is able to pack chromatography columns based on determining slurry concentration, determining column volume and determining the compression factor. These determinations enable the user to calculate the volume of the slurry needed to pack a particular chromatography column at a particular bed height. Once these determinations have been made and entered into a control unit, a computer, or a computer-like processor, which controls all critical components of the column packing system, the control unit can then execute the column packing procedure in a completely automated fashion without any interference whatsoever or assistance by and from the user. The absence of human interference and/or assistance during the column packing procedure ensures the decrease of all errors associated with such interference and/or assistance, and provides for the accurate and reproducible packing of chromatography columns. Thus, this invention provides the user with an automated means to pack chromatography media in chromatography columns that prevents the chromatography columns from being poorly packed.

Although the invention has been illustrated by examples of embodiments in which the column is cylindrical and has a constant diameter, which enables a linear correlation between cylinder volume and bed height, it is also conceivable to adapt the present invention for application to other column shapes in which the correlation is non-linear.

Even though the present invention has been described above in terms of specific embodiments, many modification and variations of this invention can be made as will be obvious to those skilled in the art, without departing from its spirit and scope as set forth in the following claims.

What is claimed is:

1. A method for automating column packing comprising:
   determining a slurry concentration for a slurry of a chromatography medium;
   determining a column volume in a chromatography column;
   determining a compression factor in the chromatography column for the chromatography medium;
   calculating a volume of the slurry needed for packing the volume with the determined compression factor, the calculation being based on the determined column volume, the determined compression factor and the determined slurry concentration;
   configuring the calculated volume of the slurry in a slurry tank;
   positioning a movable adapter of the chromatography column at a first position;
   positioning or opening a media valve that allows for delivery of the calculated volume of the slurry into the chromatography column;
   consolidating the chromatography medium;
   automatically lowering the movable adapter to a second position in order to compress the chromatography medium to the determined compression factor; and
   automatically terminating the packing of the column by terminating the delivery of the slurry to the chromatography column when an optimal column bed height is reached.

2. The method of claim 1, wherein the optimal column bed height occurs when the movable adapter has displaced a volume of liquid equal to a difference in volume between the first position of the movable adapter and the second position of the movable adapter.

3. The method of claim 1, wherein the media valve is from the group consisting of nozzle, slurry port and slurry valves.

* * * * *